United States Patent [19]

Roberts

[11] 4,369,776

[45] Jan. 25, 1983

[54] DERMATOLOGICAL IONIZING VAPORIZER

[76] Inventor: Wallace A. Roberts, 88 N. Main St., Bellingham, Mass. 02019

[21] Appl. No.: 235,855

[22] Filed: Feb. 19, 1981

Related U.S. Application Data

[63] Continuation-in-part of Ser. No. 29,004, Apr. 11, 1979, abandoned, which is a continuation-in-part of Ser. No. 757,039, Jan. 5, 1977, abandoned.

[51] Int. Cl.³ .............................................. A61N 1/44
[52] U.S. Cl. ........................... 128/200.14; 128/202.25; 128/203.17; 219/272; 261/DIG. 65
[58] Field of Search ................... 128/399, 400, 200.14, 128/202.25, 203.17, 204.17; 219/272, 273, 360, 362; 361/227, 228; 363/18–21; 239/3, 136, 690; 137/192; 261/142, DIG. 65

[56] References Cited

U.S. PATENT DOCUMENTS

| | | | |
|---|---|---|---|
| 2,284,235 | 5/1942 | Ronzi | 128/200.14 |
| 2,635,225 | 4/1953 | Hadady | 137/392 |
| 3,035,145 | 5/1962 | Rudolph | 219/272 X |
| 3,417,306 | 12/1968 | Knak | 363/21 X |
| 3,531,737 | 9/1970 | Thakore | 363/18 X |
| 3,869,529 | 3/1975 | Follette | 261/130 |
| 3,876,037 | 4/1975 | Rath, Jr. | 137/392 X |
| 3,943,407 | 3/1976 | Bolasny | 361/229 |
| 3,987,133 | 10/1976 | Andra | 261/130 |
| 4,028,444 | 6/1977 | Brown et al. | 128/200.13 X |
| 4,051,205 | 9/1977 | Grant | 219/272 X |

Primary Examiner—Kyle L. Howell
Assistant Examiner—Angela Sykes
Attorney, Agent, or Firm—William Nitkin

[57] ABSTRACT

In an apparatus which produces and delivers water vapor upon the skin of an animate subject for dermatological purposes, circuitry monitors the fluid level of a heated container and disables the heating element thereof. When the water level drops, resistance in a temperature sensitive device drops disabling voltage to the heating element via the control circuitry. The control circuit cuts off power to the heating element and is capable of producing a warning signal. Also provided in combination therewith are a vapor ionizer and means utilizing capacitive discharge technology for stepping up voltage to a vapor ionizing electrode coil member.

1 Claim, 3 Drawing Figures

DERMATOLOGICAL IONIZING VAPORIZER

This application is a continuation-in-part of my application Ser. No. 029,004, filed Apr. 11, 1979, now abandoned, which in turn is a continuation in part of my previously filed application for an Improved Vaporizing Unit, Ser. No. 757,039, filed 01/05/77, and now abandoned.

BACKGROUND OF THE INVENTION

The present invention relates to an apparatus which creates vapor from fluid to be directed upon the skin of an animate body and in particular to an electronic fluid level sensing means and associated monitoring control and disabling circuitry in combination with a vapor ionizer and associated circuit means to step up the voltage for ionization of the vapor by rapidly pulsing low voltages.

Vaporizing apparatuses are utilized to prepare the skin of an animate subject for various dermatological operations. The apparatus heats a supply of fluid, usually water, to provide and direct a warm vapor to heat and moisten the skin of the subject to open the pores thereof.

A problem which has arisen in the art is providing an adequate means of sensing a lower water level in the container tank, which contains the supply of water, to prevent tank and heater burn-out. Some similar devices have no level-sensing means while others have utilized two electrodes imposed within the container. In prior art devices the electrodes, when water is present, conduct current through the water to complete a circuit. When water is not present, the circuit is broken whereby means for signalling such are activated. There are occasionally means to disable the heater. However, mineral deposits often times accumulate in the container. Current will often flow therethrough to complete the circuit and thus the related control electronics would sense that water was still available in the container. If distilled water is used to alleviate the mineral conductivity problem, the control electronics usually sense that water is not present due to the fact that distilled water is a very poor conductor.

SUMMARY OF THE INVENTION

The present vaporizing device employs means for sensing a low water level and means for disabling the apparatus upon detection of a low water level and a vapor ionizer.

In light of the foregoing, the present vaporizing apparatus incorporates therein sensing circuitry and related control circuitry such that a heater enabling water level sensing device, having a voltage and resistance related to temperature, will be cooled when surrounded by water and heated when the water level drops. Upon heating, control circuitry sensitive to voltage drops will disable a heater.

The water level sensing means is comprised of a thermistor-type sensing circuitry. Heater enabling voltage is applied to a thermistor in an aqueous environment which is sensitive to temperature in that the higher the temperature, the higher the resistance and the lower the voltage. Voltage sensitive circuitry is provided such that upon a prescribed drop in voltage, the circuitry will disable a heating element. It is therefore an object to incorporate a temperature-sensitive resistance device in an aqueous environment, with appropriately preset control circuitry, sensitive to voltage levels, to disable a heating element and display a warning of the same; and further to disable the entire apparatus.

The vaporizing unit of the present invention further includes means to ionize the water vapor be high voltage pulses across an electrode gap within the tube carrying the water vapor. The high voltage is provided through use of capacitive discharge into a high voltage step-up transformer.

Further features and advantages will become apparent from the following drawings and descriptions thereof.

DESCRIPTION OF THE PREFERRED EMBODIMENT(S)

Figure 1:
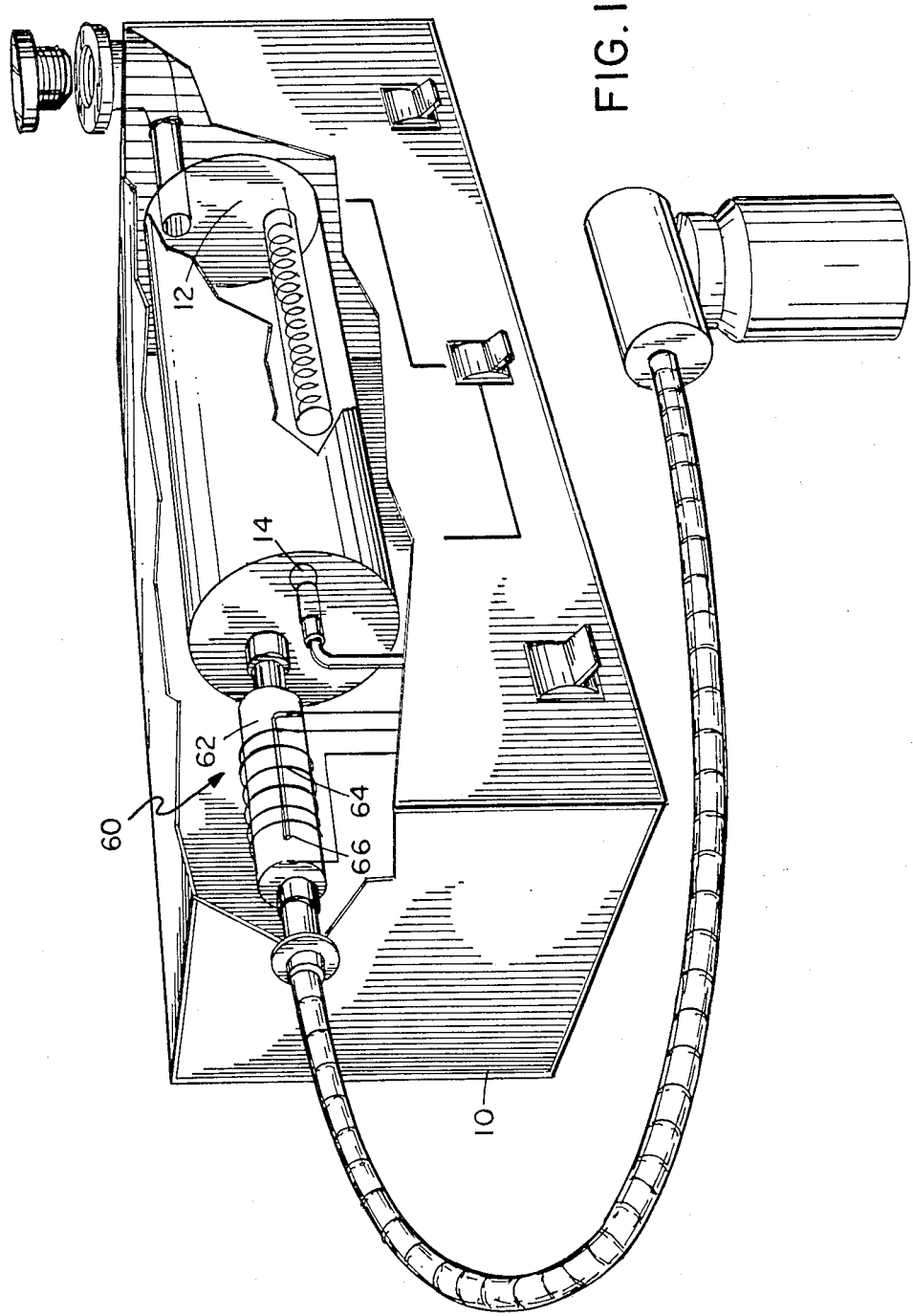
FIG. 1 is a partially cutaway perspective view of the container and water level sensing device and the related ionizing unit of this invention.

Referring to the drawings and in particular to FIG. 1, a cut out perspective view of the vaporizing apparatus 10 of the present invention, a container 12, having a water level sensing element 14 positioned therein, is illustrated. Container 12 may be of any desired configuration, but for the present application it is desired that container 10 be cylindrical. The container may be constructed of Fiberglas, a trademark for glass fibers and products made therefrom, or equivalent material. Water level sensing element 14 is embodied as a thermistor, or equivalent, and is positioned upon the interior lower surface of container 12.

The water level sensing device operates upon the principle that the aqueous medium will maintain a constant temperature and thus cause the electronic element to maintain a desired constant resistance and voltage. When the aqueous level drops below sensing element 14, the temperature of the element will rise creating greater resistance and thus less voltage which will cause monitoring and control circuitry, operating upon sensing element voltage, to indicate a low fluid level and to disable the heating element and/or the entire apparatus. Thus in the present application wherein sensing element thermistor 14 is submerged in an aqueous medium, the operating temperature range will be approximately 100° C. As sensing element thermistor 14 is exposed by low water levels, heat accumulates therein lowering conducted voltage, and the control circuitry of FIG. 2 disables the apparatus when the voltage drops below a predetermined level.

Figure 2:
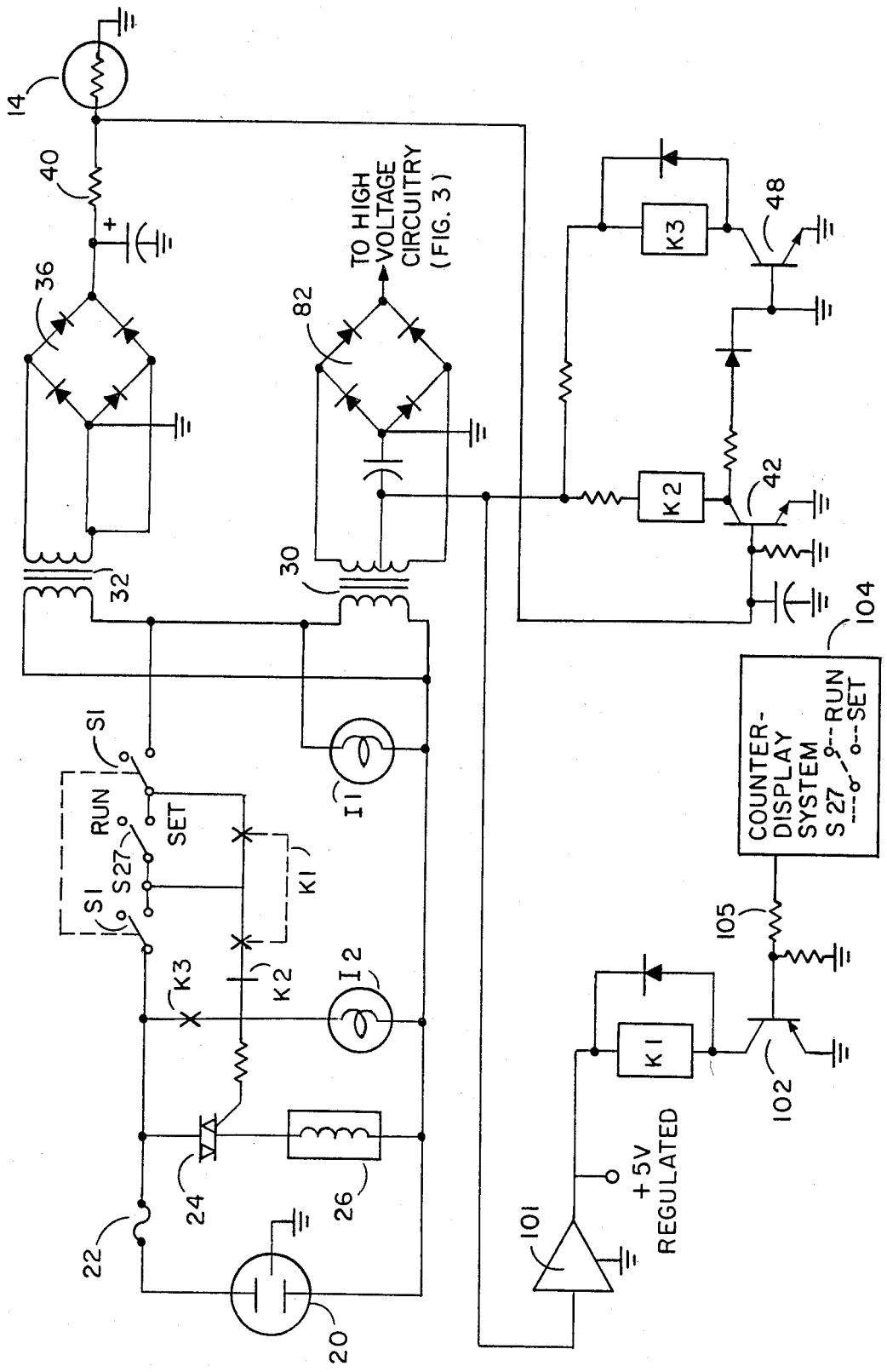
FIG. 2 is a schematic diagram of the circuitry utilized to control the heater and ionizing portions of the apparatus of FIG. 1.

FIG. 2 illustrates the preferred control circuitry of the present invention by means of a schematic diagram. Power enters vaporizing unit 10 and related circuitry through a connector 20 and fuse 22. Switch S1 is a two-pole switch that controls power to the unit. It is shown in the off position. Switch S2 is used to determine whether the unit is in the run or set mode. When the unit is in the set mode, the counter-display system 104 (which also incorporates a second pole of the switch S2) is shown in dashes as part of item 104. The following description will be made with the assumption that switch S2 is in the run mode. Power from the system is delivered to transformers 30 and 32. The presence of power is indicated by the illumination of incandescent light I1. Power from the secondary of transformer 32 is rectified by bridge 36 and is used to deliver an output that varies as a function of the temperature of thermistor 14, which is powered through resistor 40, preferably a 150 ohm, 2 watt resistor. The output from the bridge 36 is typically 16 volts. When water level in the apparatus falls below a predetermined level, thermistor 14 is exposed to heat from the heating unit 26 that is present in the apparatus. The decrease in resistance caused in the thermistor 14 decreases the voltage on the base of transistor 42 causing it to cut off and open the contacts of relay K2, which otherwise are closed when transistor 42 is conducting. The heating unit 26 is in series with a bidirectional triac 24, and opening the relay contacts K2 causes the triac 24 to open the circuit to the heater and thereby turn it off.

At the same time that the contacts of relay K2 are forced open, the contacts of relay K3 are closed, because transistor 48 is driven into conduction. The closing of contacts K3 causes the incandescent light I2 to be illuminated and indicate thereby that the water level is low.

The counter display system 104 is used in such a way as to make the heater 26 on only during a predetermined time interval that is established by setting the counter-display system. The counter-display system has an output present at point 105 that is indicative of whether the heater should be on. So long as the output is present, transistor 102 is driven into conduction, and the resulting conduction causes the contacts of relay K1 to close thereby to keep triac 24 in a conductive state. In order to set the counter-display system, the switch S2 is placed in the set position; doing so shorts out one pole of the relay contacts K1, so that the counter-display system is powered by the circuit. When this pole of switch K1 is not shorted out, it operates to disengage power from the remaining portions of the circuit at the same time that the triac 24 is put in a non-conductive state.

The transformer 30 is used to power a bridge rectifier circuit 82 that delivers unregulated power to circuits associated with relay coils K2 and k3 and regulated power to the circuit associated with the coil of relay K1. Regulation is afforded by use of integrated circuit 101 which is preferably SG309K or equivalent.

Returning now the FIG. 1 a view of vapor ionizing member 60 is illustrated. A hollow glass cylinder 62 provides the means for an electrode and for the passage of vapor. About the outer circumference of glass electrode 62 is wound wire coil 64 which is wound about cylinder 62 approximately five times. each wind spaced about 5/16ths of an inch apart. Positioned along the interior central axis of cylindrical glass electrode 62 is a straight piece of conductive wire 66 which formas a second electrode. Wire electrode 66 is appropriately grounded. A high voltage potential is applied to coil 64. The voltage arcs through glass cylinder electrode 62 to wire electrode 66 to create a spark which accomplishes the ionization.

Figure 3:
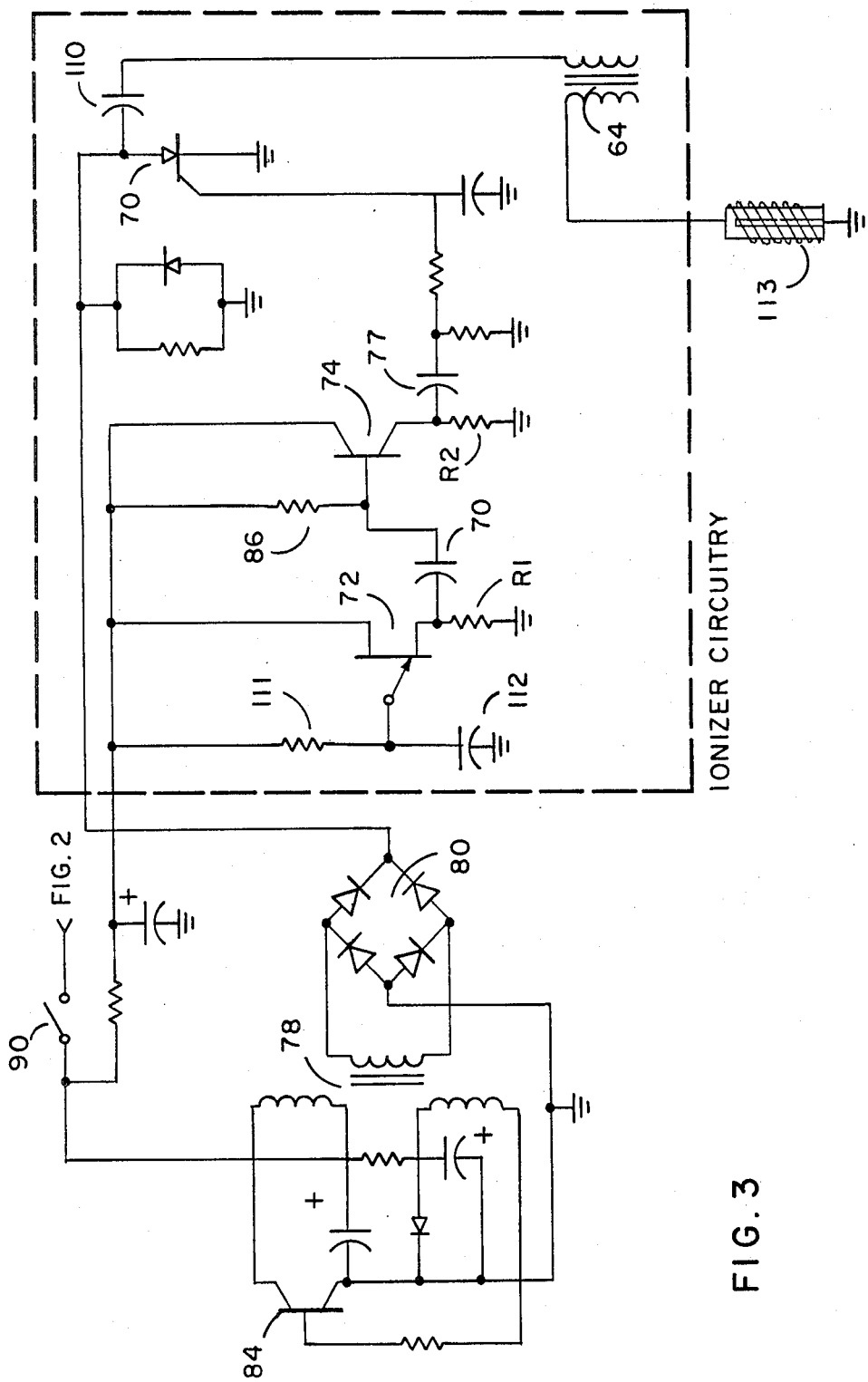
FIG. 3 is a schematic diagram of the circuitry utilized to operate the voltage step-up of the ionizer portion of the present invention.

Referring now to FIG. 3, a schematic diagram of the high voltage produced circuitry is illustrated. The circuit is similar in operation to that described, for example, in U.S. Pat. No. 3,417,306 which is hereby incorporated herein by reference. The high voltage circuitry is powered by the system including bridge rectifier group 82 shown in FIG. 2. This power is delivered through switch 90, which can be used to disable the ionizing system. Transistor 84 is used in conjunction with the primary transformer 78 to form a standard oscillator that is rectified by bridge 80. The rectified output of bridge 80 is used to charge capacitor 110 through the primary of high voltage transformer 64. The capacitor 110 is discharged through the same primary of high voltage transformer 64 when silicon-controlled rectifier 70 is triggered by the appropriate circuit.

The trigger circuitry for silicon-controlled rectifier 70 consists of a relaxation oscillator formed by the resistance-capacitance network of resistor 111 and capacitor 112 in conjuction with transistor 72. The output from transistor 72 triggers transistor 74, which in turn, fires the silicon-controlled rectifier. The high voltage output provided at the output of transformer 64 is used to energize the vaporizing coil 113. Approximately 60,000 volts of high voltage is provided by this circuit.

The foregoing description of the present invention has been illustrated with regard to a particular embodiment. However, it will be apparent to those skilled in the art that various alterations and modifications can be made and substituted therefor without departing from the spirit and scope of the following claims.

What is claimed is:

1. A dermatological ionizing vaporizer comprising:
   a. a fluid container;
   b. an electric heating coil, to vaporize the fluid within said container;
   c. delivery means to direct the vaporized fluid to the exterior of said vaporizing unit;
   d. entry means for the delivery therethrough of fluid into said fluid container;
   e. disabling means to stop operation of said heating coil when the fluid in said fluid container reaches a predetermined low level, including:
      a power source having a voltage output that decreases when put under load;
      a thermistor, positioned within a lower level of said fluid container in parallel with the power source, said thermisor being sensitive and responsive to surrounding medium temperature such that increases in temperature decrease resistance therein so as to cause voltage from the power source to decrease when temperature of the thermistor increases;
      a first transistor switch, the input of which is in parallel with the thermistor and the power source so that the input receives a temperature indicative signal that decreases with increasing temperature, such transistor normally being in a conductive state unless the temperature of the thermistor exceeds a predetermined threshold;
      a first relay having a coil in the output circuit of the first transistor switch, and contacts that are closed when the first transistor switch is in a conductive state, such contacts being opened when the first transistor switch is in a cut-off state, said first transistor switch thereby opening the contacts of the first relay when temperature of the thermistor exceeds the predetermined threshold;
      a triac, the output of which is in series with the heating coil, and the input of which is connected so as to receive power only when the first relay's contacts are closed, such triac thereby powering the heating coil only when the first transistor switch is in a conductive state and thus only when temperature of the thermistor has not exceeded the predetermined threshold;

f. means, for warning of low water level, including
   - a second transistor switch having an input connected to the output of the first transistor switch;
   - a second relay the coil of which is connected to the output of the second transistor switch, such coil being energized when the temperature of the thermistor has exceeded the predetermined threshold and the second transistor switch is in a conductive state; and
   - an electric lamp connected in series with contacts of the second relay, so that the lamp is powered when temperature of the thermistor has exceeded the predetermined threshold;

g. means for ionizing said vaporized fluid when it is traveling through said delivery means including:
   - an ionizing electrode coil member; and

- circuitry for stepping up voltage to said ionizing electrode coil member including a silicon-rectifier controlled capacitive discharge circuit; and h. means for timing operation of the unit including:
   - a counter-display system, having an output voltage indicative of whether a pre-set interval of time has expired;
   - a third transistor switch, the input of which is connected to the output of the counter-display system;
   - a third relay, having a coil in the output circuit of the third transistor switch, and capable of being actuated upon conductance of a predetermined current through the third transistor switch's output, and having normally open contacts in series with the contacts of the first relay and the heating coil, so that the heating coil is powered only during the interval timed by the counter display system.

* * * * *